United States Patent
Manion et al.

(10) Patent No.: US 9,535,043 B2
(45) Date of Patent: Jan. 3, 2017

(54) COLOR CHANGE INDICATOR OF BIOFILM FORMATION

(71) Applicant: Empire Technology Development LLC, Wilmington, DE (US)

(72) Inventors: Michael Keoni Manion, Cronulla (AU); George Charles Peppou, Hornsby Heights (AU)

(73) Assignee: Empire Technology Development LLC, Wilmington, DE (US)

( * ) Notice: Subject to any disclaimer, the term of this patent is extended or adjusted under 35 U.S.C. 154(b) by 246 days.

(21) Appl. No.: 14/130,956

(22) PCT Filed: May 31, 2013

(86) PCT No.: PCT/US2013/043546
§ 371 (c)(1),
(2) Date: Jan. 6, 2014

(87) PCT Pub. No.: WO2014/193401
PCT Pub. Date: Dec. 4, 2014

(65) Prior Publication Data
US 2014/0352602 A1   Dec. 4, 2014

(51) Int. Cl.
*G01N 31/22* (2006.01)
*A61L 29/14* (2006.01)
(Continued)

(52) U.S. Cl.
CPC ............ *G01N 31/222* (2013.01); *A61L 29/14* (2013.01); *A61L 29/148* (2013.01); *A61L 31/14* (2013.01);
(Continued)

(58) Field of Classification Search
CPC ........... G01D 7/00; G01D 7/005; A61F 13/42; C12Q 1/00; C12Q 1/04; A61L 29/14; A61L 29/148; A61L 31/14; A61L 31/148; G01N 31/222; A61M 25/0017
(Continued)

(56) References Cited

U.S. PATENT DOCUMENTS 2,485,566 A * 10/1949 Clark ................ G01N 31/221
                                              116/206
3,881,993 A    5/1975 Freake et al.
(Continued)

FOREIGN PATENT DOCUMENTS

| WO | 0024438 A1 | 5/2000 |
| WO | 2006000764 A1 | 1/2006 |
| WO | 2012061227 A2 | 5/2012 |

OTHER PUBLICATIONS

Mohan, S.K., Microbial deterioration and degradation of polymeric materials, J. Biochem Tech., 210-215 (2010).
(Continued)

*Primary Examiner* — R. A. Smith
*Assistant Examiner* — Tania Courson
(74) *Attorney, Agent, or Firm* — The Juhasz Law Firm (57) ABSTRACT

Technologies are generally described for devices for detection of a biofilm by a color change in a moisture-indicating substance, such as a chemical or a dye. The moisture indicating material may be supported by a substrate and sealed to keep moisture from the moisture indicating material. Alternatively, the moisture indicating material may be supported in a pouch and sealed by the pouch. The color change results from an ingress of moisture accompanying growth of a biofilm. The moisture-indicating substance may be used with indwelling or other devices to detect a biofilm. When the biofilm has sufficiently degraded the seal, an ingress of moisture and its accompanying pH may cause a color change in the moisture-indicating substance to signify (Continued)

the presence of the biofilm. Methods of manufacture and use of the disclosed devices are also described.

35 Claims, 4 Drawing Sheets

(51) Int. Cl.
*A61L 31/14* (2006.01)
*A61F 13/42* (2006.01)
*G01D 7/00* (2006.01)
*C12Q 1/00* (2006.01)
*C12Q 1/04* (2006.01)
*A61M 25/00* (2006.01)

(52) U.S. Cl.
CPC .............. *A61L 31/148* (2013.01); *A61F 13/42* (2013.01); *A61M 25/0017* (2013.01); *C12Q 1/00* (2013.01); *C12Q 1/04* (2013.01); *G01D 7/00* (2013.01); *G01D 7/005* (2013.01)

(58) Field of Classification Search
USPC .......... 116/200, 201, 206; 427/2.1; 422/425, 422/426; 435/4, 29, 31; 128/207, 205.23; 604/96.01, 264, 349, 544, 318, 361, 404; 600/309, 362, 310, 306, 307
See application file for complete search history.

(56) References Cited

U.S. PATENT DOCUMENTS

| | | | | |
|---|---|---|---|---|
| 4,516,679 A * | 5/1985 | Simpson | ................ | B65D 75/52 206/459.1 |
| 4,987,849 A * | 1/1991 | Sherman | ................ | B65D 79/02 116/200 |
| 5,103,817 A | 4/1992 | Reisdorf et al. | | |
| 5,317,987 A * | 6/1994 | Muller | .................... | G01K 3/04 116/206 |
| 5,679,399 A * | 10/1997 | Shlenker | ................ | A01N 25/10 128/844 |
| 5,788,687 A | 8/1998 | Batich et al. | | |
| 5,897,993 A * | 4/1999 | Sato | ........................ | C12Q 1/06 435/10 |
| 6,048,620 A * | 4/2000 | Zhong | ................... | A61L 29/085 427/2.1 |
| 6,306,422 B1 | 10/2001 | Batich et al. | | |
| 6,413,778 B1 | 7/2002 | Carpenter et al. | | |
| 6,485,978 B1 * | 11/2002 | Kirckof | .................... | A61L 2/28 422/403 |
| 6,551,346 B2 | 4/2003 | Crossley | | |
| 6,589,761 B1 * | 7/2003 | Freadman | ................ | C12Q 1/04 435/283.1 |
| 6,626,939 B1 * | 9/2003 | Burnside | ................... | A61F 2/07 623/1.38 |
| 6,793,880 B2 * | 9/2004 | Kippenhan, Jr. | ......... | A61L 2/18 422/1 |
| 7,036,452 B1 * | 5/2006 | Tester | ................... | G01K 11/06 116/206 |
| 7,105,225 B2 * | 9/2006 | Birkholz | ................... | B32B 7/12 428/343 |
| 7,682,696 B2 * | 3/2010 | Dean | ........................ | A61L 2/07 116/206 |
| 7,732,046 B2 * | 6/2010 | LaBrosse | ................ | B32B 7/12 428/343 |
| 7,743,642 B2 * | 6/2010 | Chiba | ................... | B01D 53/261 73/29.04 |
| 7,749,531 B2 * | 7/2010 | Booher | ................... | A61B 5/14539 422/401 |
| 7,824,180 B2 | 11/2010 | Abolfathi et al. | | |
| 8,003,179 B2 * | 8/2011 | Merical | .................... | B32B 7/02 206/363 |
| 8,061,292 B2 | 11/2011 | Ahmed et al. | | |
| 8,062,234 B2 | 11/2011 | Stickler et al. | | |
| 8,182,914 B2 * | 5/2012 | LaBrosse | ................ | B32B 7/12 428/343 |
| 8,425,996 B2 | 4/2013 | Gorski et al. | | |
| 8,691,264 B2 * | 4/2014 | Li | ........................ | A61K 9/0024 424/425 |
| 2002/0051861 A1 * | 5/2002 | Jennings | ................ | B65D 27/30 428/67 |
| 2003/0211618 A1 * | 11/2003 | Patel | ........................ | A61L 2/07 436/38 |
| 2004/0034121 A1 * | 2/2004 | Nozaki | .................... | C08K 9/08 523/124 |
| 2004/0253185 A1 | 12/2004 | Herweck et al. | | |
| 2005/0131356 A1 | 6/2005 | Ash et al. | | |
| 2005/0197634 A1 | 9/2005 | Raad et al. | | |
| 2005/0249899 A1 * | 11/2005 | Bonutti | .................... | B32B 27/00 428/35.2 |
| 2006/0069305 A1 * | 3/2006 | Couvillon, Jr. | ..... | A61B 1/00055 600/117 |
| 2006/0084127 A1 | 4/2006 | Ericson | | |
| 2006/0236913 A1 * | 10/2006 | Wills | ..................... | A61B 19/00 116/206 |
| 2007/0079748 A1 * | 4/2007 | Ahmed | ................... | A61L 15/56 116/206 |
| 2007/0129690 A1 * | 6/2007 | Rosenblatt | .............. | A61L 29/16 604/265 |
| 2007/0154621 A1 | 7/2007 | Raad | | |
| 2008/0085282 A1 | 4/2008 | Qiu et al. | | |
| 2009/0220378 A1 | 9/2009 | McDonnell et al. | | |
| 2009/0305331 A1 | 12/2009 | Ben-Horin et al. | | |
| 2010/0010327 A1 | 1/2010 | Merz et al. | | |
| 2010/0041753 A1 | 2/2010 | Eldridge | | |
| 2010/0150989 A1 | 6/2010 | Hoffman et al. | | |
| 2010/0233021 A1 | 9/2010 | Berman et al. | | |
| 2011/0200655 A1 | 8/2011 | Black et al. | | |
| 2011/0274593 A1 | 11/2011 | Gorski et al. | | |
| 2012/0143160 A1 * | 6/2012 | Song | ..................... | G01N 21/78 604/361 |
| 2012/0150096 A1 | 6/2012 | Li et al. | | |
| 2012/0259295 A1 * | 10/2012 | Bonutti | ................... | B32B 27/00 604/272 |
| 2013/0041238 A1 | 2/2013 | Jospeh et al. | | |
| 2013/0064772 A1 | 3/2013 | Swiss et al. | | |
| 2014/0018654 A1 * | 1/2014 | Drury | .................... | A61B 5/445 600/362 |
| 2014/0148671 A1 * | 5/2014 | Peppou | .............. | A61B 5/14503 600/367 |
| 2014/0275864 A1 * | 9/2014 | Drury | .................... | A61L 15/26 600/309 |
| 2015/0112228 A1 * | 4/2015 | Ekema | ................ | A61F 5/4408 600/584 |

OTHER PUBLICATIONS

Joshi, G.B., Development of pH Sensitive Hydrogel for Intestinal Delivery of Methyl Prednisolone Using Novel Chitosan Derivative, Int. J. Pharm. and Pharma. Sciences, vol. 3, issue 1, 200-203, (2011).
Rinaudo C.D. et al., Specific Involvement of Pilus Type 2a in Biofilm Formation in Group B *Streptococcus*, PLoS ONE 5 (2) Feb. 15, 2010, 11 pages.
Medscape 2012 Article 582018-5, Bacterial Biofilms in Patients with Indwelling Urinary Catheters: the Formation of Proteus Mirabilis Biofilms, 4 pages.
Broomfield, R.J. et al., Crystalline Bacterial Biofilm Formation on Urinary Catheters by Urease-producing Urinary Tract Pathogens: a Simple Method of Control, J. Medical Microbiology (Jun. 2009), 1367-1375.
Chandki, R. et al., Biofilms: A microbial home, J. Indian Soc. Periodontol. 15 (2) 2011) 111-114.
Int'l Search Report and Written Opinion, PCT/US13/43546, mailed Oct. 24, 2013, 12 pages.
Int'l Search Report and Written Opinion PCT/US13/43552, dated Aug. 30, 2013, 8 pages.
Int'l Search Report and Written Opinion PCT/US13/43626, dated Sep. 4, 2013, 8 pages.

(56) References Cited

OTHER PUBLICATIONS

Applied Physics Letters 70, 526 (1997), Metglas thin film with as-deposited domain alignment for smart sensor and actuator applications, Yong Lu and Arokia Nathan, 4 pages.
Biomaterials 19 (1998) pp. 1877-1884, A liposomal hydrogel for the prevention of bacterial adhesion to catheters, Valerio DiTizio et al., 8 pages.
Polymer Degradation and Stability 59 (1998) pp. 309-315, Relevance of biofilms for the biodeterioration of surfaces of polymeric materials, Hans-Curt Flemming, 7 pages.
Journal of Magnetism and Magnetic Materials, 254-255 (2003) pp. 598-602, Magnetic materials for electronic article surveillance, Giselher Herzer, 5 pages.
SPIE vol. 2459, pp. 140-148, Detection of corrosion in pipe using the magnetostrictive sensor technique, H. Kwun et al., 9 pages.
Journal of Hospital Infection 64 (2006) pp. 313-325, Bacterial biofilms within the clinical setting: what healthcare professionals should know, D. Lindsay et al., 13 pages.
European J. of Pharmaceutics and Biopharmaceutics 72 (2009) pp. 1-8, pH-Sensitive nanospheres for colon-specific drug delivery in experimentally induced colitis rat model, Abdallah Makhlof et al., 8 pages.
International Biodeterioration & Biodegradation 61 (2008) pp. 135-141, Microbiologically induced corrosion of copper pipes in low-pH water, A. Reyes et al., 7 pages.
Food Reviews International, 27:3 (2011) pp. 300-329, Microbial biosensors for Environmental Monitoring and Food Analysis, Xia Xu and Yibin Ying, 31 pages.
Proceedings of 31st Annual Int'l Conference of IEEE EMBS, Minneapolis, MN (Sep. 2009) pp. 5436-5439, Wireless, Magnetic-based Sensors for Biomedical Applications, Kent Ghee Ong et al., 4 pages.
Anaissie, E., et al., "Role of catheter colonization and infrequent hematogenous seeding in catheter-related infections," European Journal of Clinical Microbiology and Infectious Disease, vol. 14, Issue 2, pp. 134-137 (Feb. 1995).
Peter, C., et al., "Pharmacokinetics and organ distribution of intravenous and oral methylene blue," European Journal of Clinical Pharmacology, vol. 56, No. 3, pp. 247-250 (Jun. 2000).

\* cited by examiner

COLOR CHANGE INDICATOR OF BIOFILM FORMATION

CROSS-REFERENCE TO RELATED APPLICATION

The present application is a U.S. National stage filing under 35 U.S.C. §371 of International Application No. PCT/US13/43546, filed on Mar. 31, 2013.

TECHNICAL FIELD

The technical field of the disclosure relates to biofilm detection.

BACKGROUND

Biofilm formation on in-dwelling medical devices can lead to serious morbidity and mortality. Detection at the early stages of biofilm formation affords the ability to exchange the device with a new one prior to the establishment of an intractable infection and possible septicemia. There are also other applications in which biofilm contamination is highly undesirable.

The detection of biofilm in any material may provide notification that the material should be removed or replaced to mitigate the risk of contamination. However, current biofilm detection technology may be limited to complex systems.

Unless otherwise indicated herein, the materials described in this section are not prior art to the claims in this application and are not admitted to be prior art by inclusion in this section.

SUMMARY

Technologies are herein described for detection of a biofilm by a color change in a moisture-indicating substance, such as a chemical or a dye. The moisture indicating material may be supported by a substrate and sealed to keep moisture from the moisture indicating material. Alternatively, the moisture indicating material may be supported in a pouch and sealed by the pouch. The color change results from an ingress of moisture accompanying growth of a biofilm. The moisture-indicating substance may be used with indwelling or other devices to detect a biofilm. When the biofilm has sufficiently degraded the seal, an ingress of moisture, a resulting change in the pH, or both, may cause a color change in the moisture-indicating substance to signify the presence of the biofilm. pH is calculated as the negative log of the concentration of hydrogen ions in the solution. Methods of manufacture and use of the disclosed devices are also described.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Technologies are generally described for devices for detection of a biofilm by a color change in a moisture-indicating substance, such as a chemical or a dye. The moisture indicating material may be supported by a substrate and sealed to keep moisture from the moisture indicating material. Alternatively, the moisture indicating material may be supported in a pouch and sealed by the pouch. The color change results from an ingress of moisture accompanying growth of a biofilm. The moisture-indicating substance may be used with indwelling or other devices to detect a biofilm. When the biofilm has sufficiently degraded the seal, an ingress of moisture, the accompanying pH change, or both, may cause a color change in the moisture-indicating substance to signify the presence of the biofilm. Methods of manufacture and use of the disclosed devices are also described.

Figure 1:
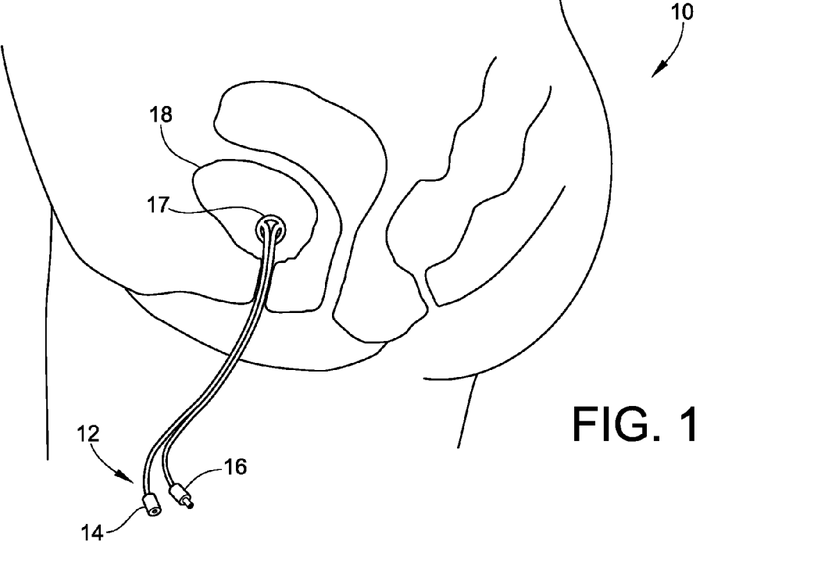
FIGS. 1 and 2 are perspective views illustrating an indwelling medical device in female and male use, respectively, according to this disclosure.
Figure 2:
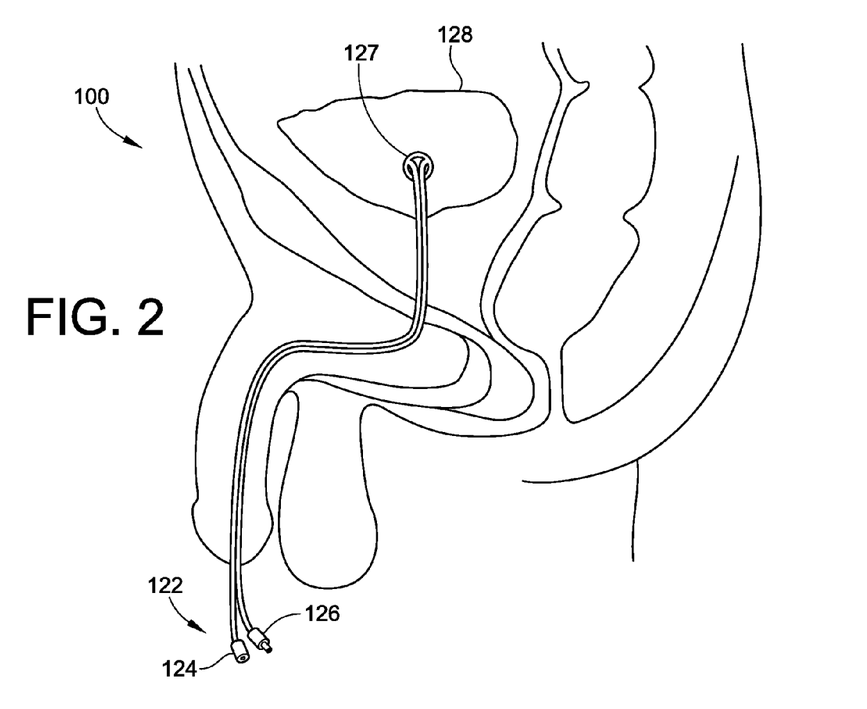

In describing more fully this disclosure, we make reference to the accompanying drawings, in which illustrative embodiments of the present disclosure are shown. This disclosure may, however, be embodied in a variety of different forms and should not be construed as so limited. FIGS. 1 and 2 respectively depict examples of female and male patients 10, 100 into which a urinary Foley catheter 12, 122 has been inserted. The catheters 12, 122 include a first portion 14, 124 for drainage of urine and a second portion 16, 126 for inflation of the retaining portion 17, 127 of the Foley catheter within the patient's urinary bladder 18, 128.

Biofilm formation in indwelling devices, such as the urinary catheters illustrated in FIGS. 1 and 2, are well established, due to the level of exposure of the region, large amounts of water present and nutrient availability the biofilm formation is common. Consequently infection risk is very high, with essentially all patients receiving long-term catheterization receiving a urinary tract infection (UTI).

A biofilm is an undesirable growth of microorganisms that may form on an object. Biofilms are particularly attracted to polymeric materials, such as plastics, because polymers are a source of carbon and energy for many microorganisms, such as bacteria and fungi.

As is well known in the art, biodegradation of a polymeric material is chemical degradation brought by the action of naturally occurring microorganisms via enzymatic action into metabolic products. Such biodegradation can lead to a complete or near complete conversion of the material components. This is in contrast to biodeterioration or biocorrosion which simply results in a change in the polymer structure. The result for both cases is a drastic decrease in molecular weight and consequently a loss of integrity. Other consequences may include formation of waste products as a result of the polymer degradation.

An example of the destructive effect of biofilms occurs in the use of medical devices which are inserted or implanted into patients. These devices may include insertable devices, such as cannulae, catheters or stents. Other devices may include implantable devices, such as prostheses. Such catheters may include urinary catheters. In addition to infections, growth of biofilms may even result in partial or complete blockage of the lumen of the catheter, i.e., occlusion of the catheter and subsequent inability of the catheter to drain the bladder. This condition requires removal and replacement of the catheter, which may cause a great deal of discomfort to the patient. If the biofilm were detected earlier, i.e., before occlusion occurs, the catheter or other device could be removed and replaced with much less difficulty.

Biofilm formation in urinary catheters is well established. Biofilm formation is common due to the level of exposure of the region, the large amounts of water present and nutrient availability. Consequently infection risk is very high, with essentially all patients receiving long-term catheterisation receiving a UTI. The mechanisms of colonisation and infection have been described. When a biofilm is allowed to grow in an inappropriate place, the drainage lumen may be partially blocked, impeding the flow of urine, or completely occluded. Measures taken in the prior art to prevent crystallisation including silver coatings and antibiotic impregnated materials have been shown to be ineffective in preventing biofilm formation. Novel approaches to prevention are welcome due to the high health care costs, particularly in the United States, associated with treatment of catheter-acquired infections.

Occlusion of the catheter lumen is the most serious consequence of colonisation of the urinary catheter, in which bacteria capable of producing urease convert the abundant urea into ammonia, raising the pH. Species known in the prior art are capable of raising the local pH to above 8.0. At this high pH, calcium and magnesium phosphate in the urine may crystallize on the wall of the catheter. This process is rapid and can occlude the catheter in as little as 40 hours. Consequences of occlusion are severe, as the catheter may be contaminated by several species of bacteria while simultaneously being occluded. Infection is inevitable under these conditions; while urinary infections may be fatal, this is thankfully a rare outcome. The occlusion instigates urinary retention. If the catheter remains in place, this can lead to reflux of infected urine into the kidneys, resulting in pyelonephritis and septicaemia. If this occurs, the patient is likely to spend a greater amount of time in the hospital, increasing overall healthcare cost.

Having thus introduced background on implantable devices, such as urinary catheters, we now turn to features that are provided by this disclosure.

Technologies are generally described for devices for detection of a biofilm by a color change in a moisture-indicating substance, such as a chemical or a dye. The moisture indicating material may be supported by a substrate and sealed to keep moisture from the moisture indicating material. Alternatively, the moisture indicating material may be supported in a pouch and sealed by the pouch. The color change results from an ingress of moisture accompanying growth of a biofilm. The moisture-indicating substance may be used with medical indwelling or other devices to detect a biofilm. When the biofilm contacts the moisture indicating material, an ingress of moisture and its accompanying pH change may cause a color change in the moisture-indicating substance to signify the presence of the biofilm. Methods of manufacture and use of the disclosed devices are also described.

Figures 3, 4, 5, 6:
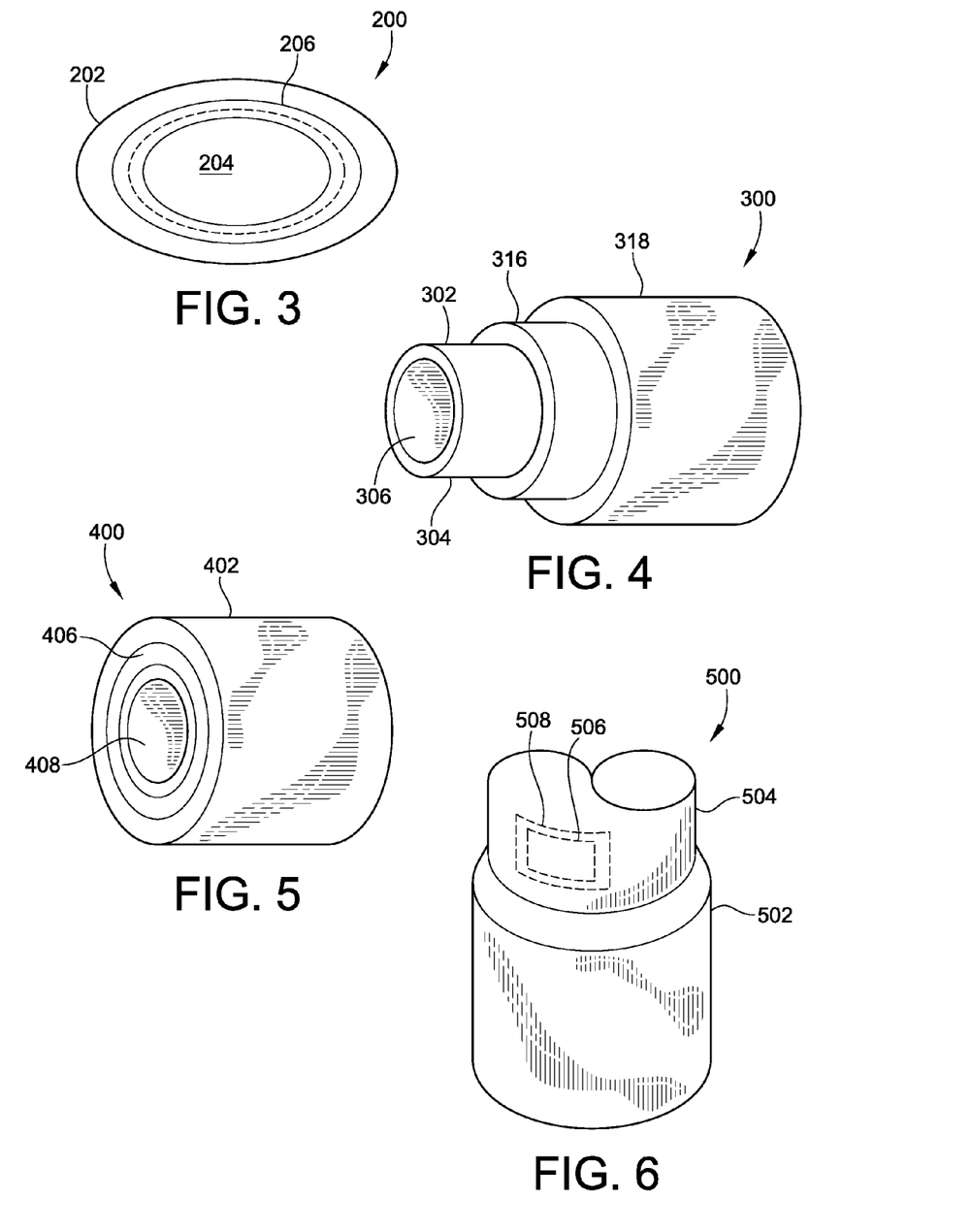
FIG. 3 is a cross sectional view illustrating a first embodiment with a layer of an indicator material combined with a transparent polymer.
FIG. 4 is a perspective exploded view illustrating a first embodiment of a substrate with an indicator material and a sealing layer.
FIG. 5 is a perspective cross-sectional view of a second embodiment of a substrate with an indicator material and a sealing layer.
FIG. 6 is a perspective view illustrating a container with an indicator material and a sealing layer.

In a first embodiment illustrated in FIG. 3, a single layer 206 provided on a substrate object 202 is configured to indicate the presence of a biofilm. A moisture indicator material and a biodegradable polymer are advantageously combined to form this single layer 206. This two component make-up of the single layer 206 of this disclosure is graphically depicted in FIG. 3 by the phantom line showing the single layer 206 as formed from two portions. The biodegradable polymer provides a substrate for holding the moisture indicator. The moisture indicator is a color-changing material, such as a chemical or dye which changes color in the presence of moisture. The chemical or dye may thus make an abrupt and noticeable change in color to signal that moisture is present.

In an alternative embodiment, the single layer 206 may be provided with a sealing layer in a manner described in detail later in this disclosure. The seal provides some protection of the moisture indicator material from the environment. When the seal is broken, as by a biofilm, the ingress of moisture will trigger the moisture indicator material to change color; thereby indicating that moisture has penetrated the seal. This color change signals that moisture is in an area where it is not desirable. Examples of abrupt color changes include a change from yellow to deep blue, or from sky-blue to deep purple. These and other color changes are described in greater detail below. In the example of a single layer 206 according to this disclosure shown in FIG. 3, the substrate 202 or object on which single layer 206 is disposed is illustratively an insertable or implantable medical device, such as a catheter 200, which may have a tubular body with an inner hollow passageway or lumen 204. In this embodiment, the passageway is coated with the single-layer coating 206 which includes the moisture-indicating substance and the biodegradable polymer, as previously described and as disclosed in greater detail below. Alternatively, the single layer 206 may be applied to a package, a piece of equipment, or other desired substrate or package where the detection of moisture is desirable. Other applications of the single layer 206 will be apparent to one skilled in the art from this disclosure. When moisture comes into contact with the moisture indicator of the single layer 206, a color change is triggered; indicating the presence of a biofilm, such as the contamination of the single layer 206 by a biofilm. Appropriate action can be taken in response.

FIG. 4 is a perspective exploded view illustrating a first embodiment of a substrate with an indicator material and a sealing layer. More specifically, FIG. 4 illustrates a device 300, illustratively, an indwelling device used as a substrate and having an outer surface with the coatings of the present disclosure. The device 300 includes a substrate 302; an indicating material 316 disposed on the substrate, the indicating material comprising a hydration indicator; and a sealing layer 318 disposed on the indicating material, the sealing layer comprising a biodegradable polymer that seals the indicating material from moisture. In this example device 300, substrate 302 depicts a coated catheter substrate having an outer surface 304 and an inner lumen 306, such as a lumen for removal of urine or passage of other body fluid. In this embodiment, the outer surface 304 is coated with the indicating material 316 shown as a first layer that includes a moisture indicating substance and a binder, which may be a hygroscopic material. Sealing or outer layer 318 shown includes a transparent biodegradable polymer which is designed to be breached by a biofilm, the breach allowing fluid to penetrate outer layer 318 and subsequently to reach first layer 316.

As used herein, an "indwelling medical device" is an implantable or insertable medical device. Non-limiting examples of indwelling medical devices include, but are not limited to, angiographic catheters, balloon catheters, biomedical implants, cardiac catheters, cardiac catheter-microphones, central venous catheters, condom catheters, contact lenses DeLee catheters, double-channel catheters, elbowed catheters, electrode catheters, endotracheal tubes, female catheters, fluid-filled catheters, Foley catheters, Gouley catheters, Gruentzig balloon catheters, indwelling catheters, intrauterine devices, mechanical heart valves, needleless connectors, pacemakers, pacing catheters, peritoneal dialysis catheters, prostatic catheters, prosthetic joints, self-retaining catheters, snare catheters, stents, Swan-Ganz catheters, Tenckhoff catheters, toposcopic catheters, two-way catheters, tympanostomy tubes, ureteral catheters, urethral catheters, vascular catheters, voice prostheses, winged catheters.

A non-limiting example of an indwelling medical device is a catheter. As used herein, a "catheter" is a medical device that is inserted into a cavity of the body typically to withdraw or introduce fluid. The catheter typically includes a shaft which may contain one or more lumens. The catheter may be inserted into a subject for introduction of fluids, for removal of fluids, or both. The subject may be a vertebrate subject such as a mammalian subject. Examples of mammalian subjects include a human, a dog, a cat, a horse, etc. Catheters may be soft catheters which are thin and flexible or may be provided in varying levels of stiffness depending on the application. Catheters may be inserted in the body to treat diseases or perform a surgical procedure. A catheter may be an indwelling catheter left inside the body, either temporarily or permanently as a permcath. By modifying the material or adjusting the way catheters are manufactured, catheters may be tailored for a wide range of medical uses including cardiovascular, urological, gastrointestinal, neurovascular, ophthalmic, and other medical applications. Some commonly used catheters include peripheral venous catheters, which may be inserted into a peripheral vein, usually in the hand or arm, for the administration of drugs, fluids, and so on. Some other illustrative examples of catheters have been previously described.

As used herein, a catheter may include various accessory components, subassemblies, or other accessory parts. For instance, a catheter may include molded components, overmolded components, subassemblies, or other accessory components or parts. The catheter may also include connecting fittings such as hubs, extension tubes, and so on. Various catheter tips designs are known. These designs include stepped tips, tapered tips, over-molded tips and split tips for multi-lumen catheters, and so on.

The shaft of a catheter may include one or more factors to increase its performance. These factors may include an antimicrobial factor, an antifouling factor, enzyme factors, factors to reduce pH, factors to solvate crystals, and so on. The shaft of a catheter may also be provided with a coating that may be provided with one or more of these factors.

Antimicrobial factors may include drugs, chemicals, or other substances that either destroy microbes, prevent their development, or inhibit their pathogenic action. Antimicrobial factors may include antibacterial drugs, antiviral agents, antifungal agents, and antiparasitic drugs.

Antifouling factors which may be released concurrently with the dye include, but are not limited to the follow classes: antibiotics, oxidising agents (e.g. iodine, peroxide), alcohol, bacteriocins, chelating agents, NaCl, $CaCl_2$, $MgCl_2$, surfactants, urea and/or antimicrobial peptides (AMPs). Furthermore, the surfaces of the devices could be antimicrobial surfaces, which can be accomplished by embedding silver, copper, or the quaternary ammonium compound 3-(Trimethoxysilyl)-propyldimethyloctadecyl ammonium chloride (Si-QAC), or other oligodynamic or antimicrobial factor. Also, the antimicrobial nature of the surface may be enhanced by modifying a physical factor such as a surface smoothness or a hydrophobic property to prevent adhesion.

Another non-limiting example of an indwelling medical device is a stent. As used herein, a stent is a mold or a device of suitable material used to provide support for structures for holding one or more biomaterials or biostructures in place. These biomaterials and biostructures may include skin, arteries, bodily orifice or cavity, or other biomaterial or biostructure of the body of the subject into which the stent may be placed. Illustrative stents may include biliary, urethral, ureteral, tracheal, coronary, gastrointestinal, esophageal stents, and so on. Stents may be used to treat coronary artery disease, problems in the peripheral vascular system, bile ducts and biliary tree, kidney, urinary tract, trachea, and bronchi. Stents may also be used to treat other medical conditions. The stents may be of any shape or configuration. The stents may include a hollow tubular structure, which may be useful in providing flow or drainage through ureteral, biliary, or other lumens. Stents may be coiled or patterned as a braided or woven open network of fibers, filaments, and so on. Stents may also include an interconnecting open network of articulable or other segments. Stents may have a continuous wall structure or a discontinuous open network wall structure.

As used herein, a stent may include a stent cover which may include a tubular or sheath-like structure adapted to be placed over a stent. The stent cover may include an open mesh of knitted, woven or braided design. The stent may be made of any material useful for providing structure for holding one or more biomaterials or biostructures in place. These materials may include metallic and non-metallic materials. They may also include shape memory materials. Metallic materials may include shape memory alloys such as nickel-titanium alloys. They may also include other metallic materials such as stainless steel, tantalum, nickel-chrome, cobalt-chromium, and so on.

Illustratively, material for making the catheter may be a polyvinyl chloride generally referred to by the abbreviation PVC. Alternatively, materials may illustratively be selected from various grades of biocompatible materials including plasticizers, silicones and latex rubbers. As used herein, the term "biocompatible" means a material that is not substantially toxic to the human body and that does not significantly induce inflammation or other adverse responses in body tissues.

The shaft of a catheter may be made using techniques commonly known in the catheter art. For example, the shaft may be formed by extrusion, such as by a thermoplastic extrusion or a thermoset extrusion as is well known in the catheter art. A coating process such as solvent casting may also be used to form the shaft.

The shaft of a catheter may include one or more color-indication materials such as dyes. The shaft of a catheter may also be provided with a coating that may be provided with one or more of color-indicating materials 316 as described below.

Continuing the discussion of FIG. 4, the indicating material 316, comprising a hydration indicator, allows a visual, color change when contacted by moisture and the pH of the moisture. Color-indicating materials for use as the indicating material 316 illustratively includes a dye. Alternatively, the indicating material may include color indicating materials whose changes are visible or not visible to the eye. Non-visible color-indicating materials may include biocompatible fluorescing dyes, with dye selection depending on the intended use. For example, where the dye needs to be viewed through tissue, dyes illustratively having a wavelength that is near or within the infrared range may provide good transmissibility for passing through tissue. In order to view dyes with an emission wave band outside of the visible spectrum of waves, energy must be delivered to the dye to excite the molecules and the resulting emission by the molecules must be collected by specialized equipment sensitive to this non-visible band of waves. Various methods and devices may be used for delivering light energy to dyes with emission outside the visible band of waves and for detecting the wavebands emitted by the dyes in response to such excitation and energy.

The indicating substances may be selected from chemical compounds or dyes which change color upon exposure to moisture. Typically, exposure to moisture causes a change in the pH or the compound's state of hydration, resulting in a visually-perceptible change of color. For example, cupric chloride exists in its anhydrous form in a light brown to yellow color, but changes upon hydration to a blue to green color as the dihydrate. Cobalt chloride appears as a beautiful sky blue color in its anhydrous form, but change to a deep purple color when it changes to the hexahydrate form upon hydration. Many dyes that are used for pH indication may be used as color-indicating compounds in applications of the principles described herein. For example, phenolphthalein changes from colorless to an orange color in an acidic environment, or to a pink-to-fuchsia color in a basic environment (pH 8-12 or above). Other chemicals used in making litmus paper for chemical analyses may also be used. In general, litmus-type chemicals turn red in an acid environment and blue in an alkaline environment.

Food dyes may also be used, such as FDC Yellow No. 5, Yellow No. 6, Red No. 3 and 40, Blue No. 1 and 2, Evan's blue, Green No. 3, β-carotene, rifampin, tetracycline, lycopene, Betanin, methylene blue and indocyanine green.

Other dyes may also act as color indicating substances, such as m-cresol purple, thymol blue, Tropaeolin OO (acid orange 5), p-xylenol blue, bromocresol green, bromocresol purple, m-cresol purple, cresol red, chlorophenol red, bromothymol blue, phenol red, cresol red, methyl red, Reichardt's dye, Morin hydrate, disperse orange 25, Nile Red, bromopyrogallol red, bromoxylenol blue, bromophenol blue, amongst many others. annatto, chlorophyllin, cochineal, Cochineal red, curcumin, riboflavin, tartrazine, quinoline yellow, carminic acid, Azorubine, Amaranth, Erythrosine, Allura Red AC, Patent Blue V, Indigotine, Brilliant Blue FCF, Green S, Brilliant Black BN, Vegetable carbon, Capsanthian, Beta-apo-8'-carotenal, Ethyl ester of beta-apo-8'-carotenoic acid, Lutein, canthaxanthin, and anthocyanins. An example of an anthocyanin is the substance extracted from red cabbage leaves; this particular anthocyanin, when used in a pH paper, is blue in a neutral environment but will turn bright pink in an acid environment and green in a basic environment.

Iridiphores, which may be used with this disclosure, are pigment cells that reflect light using plates of crystalline chemochromes. When illuminated, they generate iridescent colors because of the diffraction of light within the stacked plates. Wetting of concentrations of iridiphores will disrupt the order of the stacked plates and the light that is reflected will be different because of the difference in diffraction of the added moisture. Thus, iridiphores may also be useful as moisture indicators in the present disclosure.

Color-indicating materials 316 illustrated in FIG. 4 as the substrate-contacting first layer may include a moisture-indicating material, such as a dye, and may also include a binder, such as a hygroscopic material, to contain the dye or other moisture-indicting material. The binder should also be generally recognized as safe, and should be inexpensive. The binder may function additionally as a wetting agent or to absorb atmospheric moisture, or both. If the biofilm forms on the part of the device embedded within the patient, then the moisture will likely come from the interstitial fluid surrounding the breach engendered by the biofilm. However, if the biofilm forms on part of the device outside of the body, it will need to absorb moisture from the environment. Thus, the binder may serve as a hygroscopic agent to draw moisture into the device from the atmosphere. Some examples of materials which may be suitable may include starch based and other cellulose based binders such as carboxymethylcellulose (CMC), polyvinylpyrrolidone (PVP), hydroxyl-propylmethylcellulose, and similar materials.

It will be appreciated that any suitable color-indicating material, such as a chemical or a dye, may be used in conjunction with the present disclosure, so long as it is effective for detection directly or indirectly. Direct detection may include a visual detection. Indirect detection may be accomplished with the assistance of a machine or apparatus, or by a test on a fluid specimen containing the chemical or a dye involving a chemical or other reaction. The materials should not be unduly unsafe for the subject. Combinations of color-indicating materials may also be used, according to this disclosure. Those skilled in the art will recognize that chemical or dyes other than those listed herein can be used so long as they are effective for detection directly, such as visual detection, or indirectly, such as with the assistance of a machine or apparatus or by a test on a fluid specimen containing the dye involving a chemical or other reaction, and is not unduly unsafe for the subject.

Continuing with the discussion of FIG. 4, disposed on the indicating material is sealing layer 318. Sealing layer is illustratively, a layer of PVC. The biodegradable polymer is durable enough to withstand physical forces likely encountered by the device in normal use. The outer polymer layer is also designed to be breached by growth of a biofilm. As the biofilm grows and degrades the polymer layer, water is allowed to reach the layer with the moisture-indicating compound, which then changes its color. As the biofilm grows, more and more water penetrates the device, and greater and greater proportions of the first layer change color. The color change is visible through the layer of transparent, biodegradable polymer. The color change thus provides a clear signal that biofilm formation has occurred and that the device should be replaced. The moisture indicating material should be a material that is generally recognized as safe by medical and regulatory authorities when the material is used at appropriate levels and applications inside a person's body. The biodegradable polymer should also be one generally recognized as safe and suitable for implantation or insertion into a body of a person or other subject.

Sealing or outer layer 318 seals the color-indicating materials 316 shown as the first or substrate-contacting layer in FIG. 4 within a waterproof, transparent thin layer of polymer. This layer needs to be sufficiently strong to withstand normal handling and placement in the patient without breaching, which would cause a false positive. However, the layer should be sufficiently sensitive to degradation by biofilm formation so that it ruptures soon after significant biofilm formation, thus preventing false negatives. Suitable polymer materials for coating include FDA approved safe polymers such as polylactic acid (PLA), polyvinylacetate (PA), polycaprolactone (PCL) and polyvinyl chloride (PVC).

Other suitable polymers may also be used. More than one polymer, or a combination, may also be used. Other suitable transparent, biodegradable sealing materials may be used. Alternatively, the polymer used may be a non-transparent, biodegradable polymer, such as an opaque poly-ethylene or PVC. In this configuration, biodegradation of the polymer through the activity of the biofilm will expose the inner color-displaying layer to be exposed for the user to observe. Contact of the inner color-changing layer with moisture will trigger the color change, indicating that the moisture proof integrity of the polymer layer has been compromised. In another embodiment, an opaque plastic or other housing material may be provided with a window of a transparent, biodegradable polymer with the color changing material in accordance with this disclosure. These and other polymers for use with this disclosure may be mixed with other agents such as starch, or added as a polymeric plasticizer in other resins.

FIG. 5 depicts another device 400 suitable for insertion or implantation into a patient, such as a person, or a subject, which may be a mammal or other veterinary specimen. In FIG. 5, device 400, such as a urinary catheter, includes a substrate 402 whose inner lumen is coated with a first layer 406 having an indicating substance and a second, innermost layer 408. Innermost layer 408 includes a transparent biodegradable polymer which is designed to be breached by a biofilm, the breach allowing water to penetrate exposed layer 408 and subsequently reach indicating layer 406.

In one method to for detecting the presence of a biofilm, a first layer with a moisture-indicating compound is coated across the surface of the device, such as the catheters described in FIGS. 1-5. The layer that is adjacent to the substrate may optionally include a hygroscopic material to draw water to the moisture-indicating compound. This coating is then sealed in a thin layer of a biodegradable, transparent polymer. Both layers may extend on an outer surface, an inner surface, or across an entire surface of the device, i.e., both the inner and outer layers, or portions thereof. In other embodiments, a small spot of the moisture-indicating material may be placed on an outer surface of an object, such as a catheter by painting, extruding, or otherwise applying a quantum of the material to an external surface. The spot or quantum may then be covered and sealed with a biodegradable transparent polymer.

The method of coating the sealing layer onto a substrate may require a dry technique, such as various film forming processes which are commonly used. Spraying or brushing can be used to adhere a low viscosity liquid coating of the polymer over the dye layer followed by curing to the specifications desired specifically in terms of thickness. One desirable range of thickness extends from 0.5 microns to 500 microns (0.5 mm). In other embodiments, the dye layer may be from about 50 microns to 2 mm thick. Other thicknesses may also be used. The thickness of the coating on the outside of the device, such as an outer surface of a urinary catheter, should not interfere with the placement of the device within the patient. The thickness of the coating on an inner surface of the device, e.g., on the lumen of the urinary catheter, should not interfere with drainage or flow of fluid from the patient.

Coating devices in this way and observing the color change provides a clear signal that a biofilm has established on the device. This technique may also be combined with strategies for preventing and treating biofilms as well. For example, nanotexturing of the polymer coating may be applied to provide for an inhospitable environment for the biofilm to grown on the surface. Similarly, antimicrobial agents may be included in or on the surface and/or within the dye layer to cause a biocidal effect upon contact with microbes. In this way, a wholistic management approach to biofilm infection is taken, with detection being one of the several tools used.

Devices are individually packaged and sterilised per the normal manufacturer's protocol. The implantable or insertable devices are used in normal manner by healthcare professionals and are operated in the same way. The difference is that upon breach of the polymer layer, and consequently a color change in the moisture-indicating layer, the device provides a clear signal to the patient and/or healthcare provider that the device should be changed. Thus, instead of changing devices at regular intervals or upon inflammation (a late signal), the device is checked at least daily for this color change and swapped at the first sign of biofilm formation.

Example 1

Several examples of the application of this technology to these devices are herein described. In one embodiment, an outer surface of a Foley catheter is coated with a 1 mm thickness of a moisture-indicating layer. The moisture indicating layer is prepared from a carboxymethylchitosan hydrogel with 10% w/v (weight of solute per volume of solvent, i.e., mass concentration) bromocresol green, with a pH stabilizer (i.e., a buffer or a stabilizer of pH level which is the measure of the acidity of a solution and is calculated as the negative log of the concentration of hydrogen ions in the solution), such as acetic acid, to maintain the pH below 3.8 in its dry state. Bromocresol green is yellow when its pH is below 3.8. In this example, the mixture of the carboxymethyl-chitosan hydrogel with 10% w/v bromocresol green and 1 N acetic acid is stirred at 5000 rpm (revolutions per minute) for 30 minutes, and then spray coated on to the outside of the catheter tubing, per FIG. 4. The devices are then maintained at room temperature for 12 hours to facilitate crosslinking before being dried under vacuum. A layer of a transparent, biodegradable polymer is then applied atop the Bromocresol green layer, such as a 100 micron layer of PLA (polylactic acid). The device is then sterilized and packaged. If a biofilm forms on the catheter and the outer polymer layer is breached, the hydrogel layer will attract moisture; when the pH rises to above 5.4, the yellow color changes to a deep blue color.

Example 2

In a second example, a carboxymethylchitosan hydrogel is prepared containing the dye Betanin and is applied to a catheter. The catheter is dip-coated in PLA (polylactic acid) to provide a uniform coating over the entire dye surface to a thickness of 100 micron. This thickness may extend over both the outer surface, as shown in FIG. 4 and the inner surface of the inner lumen, as shown in FIG. 5. Carboxymethylchitosan was prepared in accordance with protocols described in the prior art. Loading of dye into a hydrogel is achieved by preparing a solution of carboxymethylchitosan in 0.1N (equivalents per liter) acetic acid and Betanin 10% (w/v) (weight of solute per volume of solvent, i.e., mass concentration). The mixture is stirred at 5000 rpm (revolutions per minute) for 30 minutes. Carbopol 934 (a crosslinked polyacrylate polymer) was prepared in 1.75 M (molar) acetic acid, and the carboxymethylchitosan is then gradually added to the Carbopol solution, the pH maintained below pH 4 (i.e., pH below pH 4 is the measure of the acidity of a solution and is calculated as the negative log of the concentration of hydrogen ions in the solution). The solution is then spray coated onto the catheters, the color of the coating a bright bluish red. The catheters are then maintained at room temperature for 12 hours to facilitate crosslinking before being dried under vacuum. Following application of the Betanin layer, the catheters are then coating in PLA to provide a uniform coating over the entire moisture-indicating surface to a thickness of about 100 microns (micrometers). Later, if a biofilm breaches the sealing polymer layer, the hydrogel layer will attract moisture. The pH of the inner layer will turn from blue-red to blue-violet as the pH increases from below 4 to neutral; if the inner layer becomes alkaline, above pH 7-8, the color will become yellow-brown.

The above teachings and examples are intended to highlight the utility of the present disclosure for medical devices. However, the present disclosure has additional advantages in other fields. Since the moisture-indicating layer provides a visual cue to the presence of a biofilm, the discovery may be applied to virtually any situation in which it is desirable to detect a biofilm. Thus, applications may be found in packaging for the medical devices and prostheses described above, as well as packaging for medicines, food packaging, and susceptible surfaces, such as the surfaces of benches, laboratory benches, laboratory equipment, and so forth.

FIG. 6 depicts a container, such as a front portion 500 of a package for a medical device or for medicine, with a moisture-indicating material and a sealing or barrier layer. Package front portion 500 includes an outer surface 502 and an inner surface 504. The inner surface includes an inner layer 506 that includes a moisture-indicator material and may include a starch or another moisture-attracting substance, such as the celluloses and hydrogels described above. The outer layer 508 is a sealing layer. In this embodiment, the sealing layer need not be a transparent layer, since the moisture-indicating layer may be visible from the outside of the package. Thus, the biodegradable polymer in this application may be transparent, semi-transparent, or opaque. Examples of such materials include opaque or semi-transparent polyethylene and polypropylene, polystyrene, and many others. These materials should be biodegradable in order to work in these applications. A quantum of the moisture-indicating layer may be applied to the substrate and sealed with a biodegradable polymer. In one embodiment, the moisture indicator has a surface area of about 1 cm$^2$. In other embodiments, the area may be larger or smaller.

The package front portion 500 may be a transparent PVC blister pack for a medical device, or it may be made from any other suitable transparent packaging material, such as polyethylene, PET (polyethylene terephthalate), acrylics, clear polystyrene, and so forth. The packaged device may be a scalpel intended for multiple uses, or the packaged device may be intended to package a catheter or a guide wire, a medical device intended for one-time use. Medical personnel can tell at a glance whether a biofilm has formed by inspecting the moisture indicating layer. If the color has changed from the as-packaged, original color, which may be indicated on the package, the user knows that at least moisture has infiltrated the package. The device can then be sterilized before use or disposed of and a replacement used instead.

The package may alternatively be a plastic or glass package for a dry food or medicine, positioned out-of-reach of the contents of the package. If the moisture-indicating layer has turned to a different color, the consumer can be aware that the contents may not be safe for use.

Figure 7:
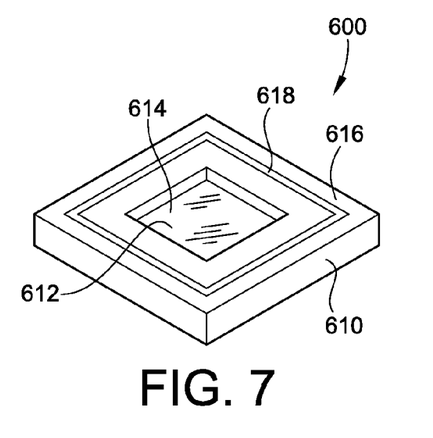
FIG. 7 is a perspective view illustrating a quantum of an indicating material in a polymeric package for application to a substrate.

In another embodiment, as disclosed in FIG. 7, a moisture-indicating label or tag 600 may apply a discrete amount or quantum of the moisture-indicating layer in a tiny container made of a biodegradable polymer. As shown in FIG. 7, a tiny pouch 610 has an small inner hollow or void 612 suitable for holding a small quantity 614 of the moisture-indicating substance that was described above. Pouch 610 is made of a biodegradable polymer, as also described above. The moisture-indicating material may include a dye or moisture-sensitive material. The moisture-indicating material may also include a binder to hold the moisture-indicating material, such as the cellulosic materials and hydrogels described herein. Moisture-indicating label 600 may be applied to a substrate by curing or crosslinking the biodegradable polymer container 610 to the substrate. Alternatively, an outer perimeter 616 of the pouch may be furnished with an adhesive layer 618 for application to a substrate.

The substrate may be a medical device, a container, a package, a surface, or other object that is deemed subject to contamination by microorganisms that may form a biofilm and contaminate the product or surface. The pouch 610 may be a transparent, biodegradable polymer for use in situations where a backside (open side) of the tag 600 is not visible to the user or other person viewing the tag. The pouch 610 instead may be an opaque biodegradable polymer in situations where the backside (open side) of the tag 600 is visible to a user or viewer. For example, if tag 600 is applied to an inside of a blister pack, the open side of tag 600 will be visible to a person viewing the blister pack. This will hold for many applications in which the tag 600 is applied to an inside of a container, such as a container for a food, a medicine, a medical device, a medical device for insertion into a subject. Conversely, if the tag 600 is intended for application on an outside of a device, then the biodegradable polymer should be transparent. In this way, the user will be able to visually observe the change in color when the polymer protective covering is breached by a biofilm and moisture ingresses into the tag 600.

Figure 8:
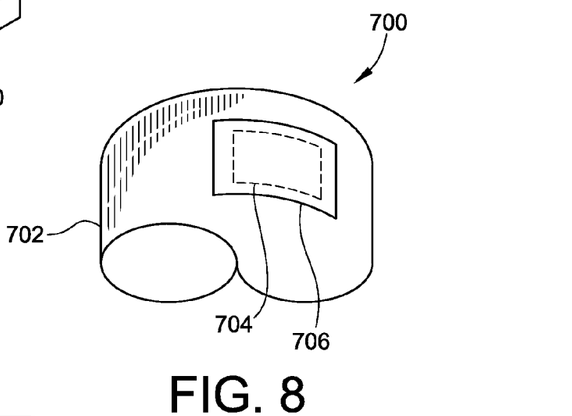
FIG. 8 is a perspective view illustrating a surface of a piece of laboratory equipment with an indicator material and a sealing layer.

Another application is disclosed in FIG. 8. In this application, a piece of laboratory equipment which may be subject to contamination is provided with an indicator material and a sealing layer. Medical laboratory microscope base 700, which may be used by several personnel on a given day, may be contaminated by fingers or gloves of a user. Thus, a surface 702 of the base, which is likely to be handled and touched by each user, is provided with a moisture-indicating layer 704 and is both sealed and adhered to the surface 702 with an outer polymer layer 706. The outer polymeric sealing layer is biodegradable by biofilms that may attach to layer 706 as laboratory personnel use the microscope and inadvertently contaminate it. If the moisture indicating layer turns color, personnel are alerted that it is time to clean or decontaminate the microscope or other laboratory equipment.

Figure 9:
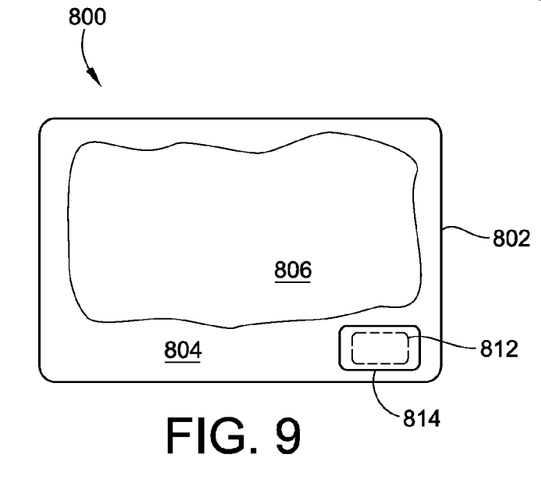
FIG. 9 is a frontal view of an embodiment of a food package with an indicator material and a sealing layer.

Another application is disclosed in FIG. 9, which depicts a food package 800, such as a supermarket meat package. Food package 800 includes a substrate 802, such as a white, opaque polystyrene tray and a clear plastic outer wrap 804 for a meat item 806. The underside of the plastic wrap 804 is furnished with a moisture-indicating layer 812 and is sealed away from the contents of the package with a sealing layer 814, as discussed above. If the food item becomes contaminated by a biofilm, the color of the moisture-indicating layer 812 will change. Supermarket personnel and customers will know that the item should not be sold or consumed.

Figure 10:
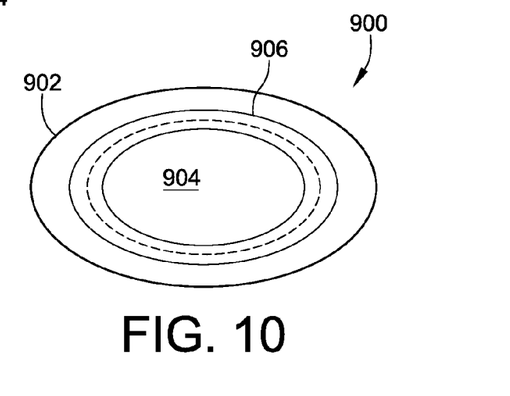
FIG. 10 is a cross sectional view illustrating an embodiment with a layer of an indicator material combined with a transparent polymer.

The above examples and illustrations concern embodiments using a two-layer biofilm indicator, the two layers including an inner moisture-indicating layer and an outer protective sealing layer that is subject to degradation by a biofilm. It is also possible to use embodiments with only a single layer, a biofilm indicator which combines the moisture indicator and the biodegradable polymer in a single layer. In embodiments using this disclosure, the indicator need not be completely sealed, as is the case in the embodiments depicted above. Instead, as shown in FIG. 10, a catheter 900 having a tubular body 902 with an inner lumen 904 is coated on the inner lumen with a single-layer coating 906. The single layer coating 906 includes both a moisture-indicating substance, as discussed above, and a biodegradable transparent polymer, as also discussed above. An example is provided for a single-layer moisture indictor as well.

A single-layer moisture indicator may be prepared in this manner and applied to a catheter, to a package or to any of the other embodiments herein disclosed. A moisture-indictor, such as a dye or a chemical, and is mixed with the transparent, biodegradable, polymer. The result is applied to a device, a substrate, a package, a piece of equipment, or other desired substrate or package. When the color changes, biofilm contamination is indicated and the appropriate action can be taken.

In this example, particles of methylene blue are formed using the vibration nozzle method. In this method, a solution of the dye and gelling agent (e.g. 3% (w/v) sodium alginate) are passed through the nozzle to generate particles of the dye. A vibration nozzle is used to generate particles of a uniform size, which may be set from 20-10,000 micron. For better results, a size of approximately 50-100 microns works well. The particles are immediately immersed in a solution to provide gelation, in the case of alginate, a 0.2 M calcium chloride solution. The particles may have a high concentration of the methylene blue, in excess of 10% (w/v).

The dye-containing particles are then mixed with PVC at a ratio of approximately 5% (w/w). An outer surface of the device, such as a catheter, may be coated by dipping or spraying. Alternatively, a tab or spot of the dye-containing PVC is applied to the desired surface, package, or other device. For example, a spot of the single-layer, moisture-indicating-material-combined-with-biodegradable polymer may be painted, extruded, or otherwise applied to an external surface. If an internal surface is desired, the compounded PVC may be warmed and applied, for instance by dipping or flowing the PVC though the tubing or fittings that will become the catheter or other device. The particles of methylene blue are dark green. When hydration occurs, the dye turns to a deep blue color.

Methods of Using the Disclosure

Figure 11:
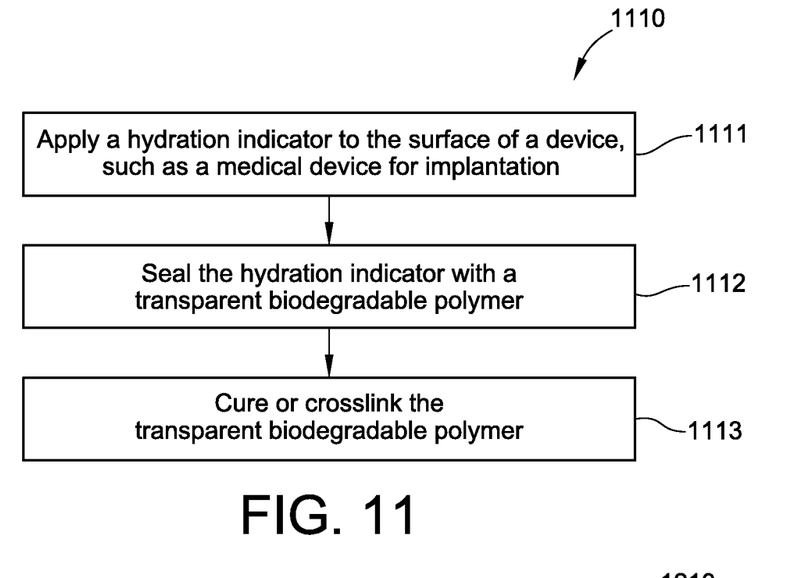
FIG. 11 is a flowchart illustrating a method of making an indwelling medical device according to the present disclosure.
Figure 12:
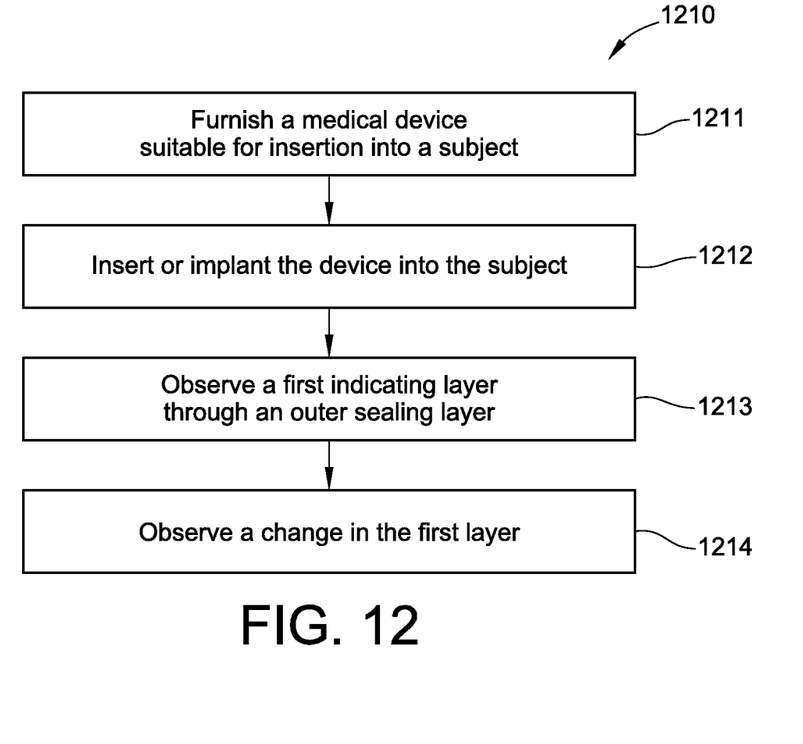
FIG. 12 is a flowchart illustrating a method using an indwelling medical device according to the present disclosure, all of the figures arranged according to at least some embodiments presented herein.

This portion of the disclosure explains two flowcharts, FIGS. 11 and 12, which depict methods of using the hydration indicator and the sealing layer, as explained above. FIG. 11 depicts a general method 1110 of using the two-layer hydration indicator in a variety of applications. In a first step 1111, apply a hydration indicator, such as a dye or other moisture-sensitive compound to a surface of a device, such as a medical device, or its package. As discussed above, the device may be a medical device for implantation into a person or a subject, or may be any of the other suitable application. In a second step 1112, seal the hydration indicator with a transparent biodegradable polymer. The third step 1113 then requires one to cure or crosslink the transparent biodegradable polymer. This step may require application of heat or pressure, or may simply require passage of an amount of time depending on the polymer used. When the polymer has formed, sealing the hydration indicator, the device or other application is ready for use. This technique may be used for many applications in which a hydration indicator and biofilm-presence indicator would be helpful, including the applications discussed above. As noted, the applications may include medical devices, medical device packaging, medicine containers, food containers or packaging, laboratory equipment and laboratory surfaces.

When the device is needed, it may be used according to method 1210, as shown in FIG. 12. In a first step 1211, the medical device, such as a catheter, may be furnished and removed from its packaging. The device is then inserted or implanted 1212 into the patient or subject. As the user goes about his or her daily activities, the device may be observed 1213. If a color of the hydration indicator layer under the transparent outer sealing layer has changed 1214, a biofilm may have formed. This alerts the patient or a healthcare provider that it may be time to replace the catheter. This method may also be used in the other applications mentioned above, to detect a biofilm.

In view of this disclosure, it will be seen that technologies are generally described for indwelling medical devices for detection of a biofilm by a color change in a moisture-indicating substance, such as a chemical or a dye. A substrate for use as an indwelling medical device is provided with an indicating material including a hydration indicator. A sealing layer is provided over the hydration layer for sealing the indicating material from moisture. When the biofilm has sufficiently degraded the seal, an ingress of moisture and its accompanying pH may cause a color change in the moisture-indicating substance. Methods of manufacture and use of the disclosed indwelling medical devices are also described.

The advantages of the method and the devices useful in carrying out the method include a projected low cost. The low cost nature of this approach ensures that the technology will be amenable to commoditized devices, such as catheters, cannulae, food, medicine, packaging, and so forth, as discussed above. A principal advantage of this disclosure in medical applications is that the hydration indicator provides a clear visual cue to a patient or to a healthcare provider. The color change provides a clear, easy-to-read indicator of biofilm formation, allowing the patient or the healthcare provider to take immediate action in most cases—because of the commodity-type nature of catheters, it is easy to remove and replace one quickly and easily and avoid the complications resulting from blockage. The early detection of biofilms is thus inexpensive and easy to use.

The visual indicators described herein may be applied to the entire device, or may be placed only on specific regions. For example, portions of the device intended to be covered by bandages need not be so treated. For medical devices, only a portion of the device that is external to the subject need be coated. For many of the packaging applications, only a small dot or square of the material is needed. As noted, the devices and techniques disclosed herein use inexpensive and available materials, such as dyes, and clear polymers that are also readily available. The materials and processes used to fabricate and apply the hydration indicators can be modified to the desired characteristics for a particular application. This will allow users to minimize false positive and false negative rates by selection of the optimal materials and processes for a particular application. As also noted above, other antimicrobial techniques and strategies may also be used in combination with the biofilm presence indicator disclosed here.

In view of this disclosure, it will be seen that technologies are generally described for devices for detection of a biofilm by a color change in a moisture-indicating substance, such as a chemical or a dye. The moisture indicating material may be supported by a substrate and sealed to keep moisture from the moisture indicating material. Alternatively, the moisture indicating material may be supported in a pouch and separately sealed or sealed by the pouch. The color change results from an ingress of moisture accompanying growth of a biofilm. The moisture-indicating substance may be used with indwelling or other devices to detect a biofilm. When the biofilm has sufficiently degraded the seal, an ingress of moisture and/or its accompanying pH change may cause a color change in the moisture-indicating substance to signify the presence of the biofilm. Methods of manufacture and use of the disclosed devices are also described.

It will be appreciated that this disclosure may be used in any situation in which introduction or growth of a biofilm is undesirable. Examples include medical devices intended for insertion or implantation into a person or other subject. Prostheses and other indwelling medical devices for implantation into a person or other subject may also benefit from early detection of biofilm formation. Biofilms also may form within packages for food, medicine, medical devices, prostheses, and the like. Equipment and surfaces in institutions that are subject to contamination, such as food processing institutions, laboratories, and compounding formularies would benefit from early detection of biofilm contamination. An inexpensive, easy-to-use and highly visible color indication would assist operators and oversight personnel avoid biofilm contamination in each of these situations.

In medical application, this disclosure may be used with any indwelling devices, such as catheters and cannulae, are low cost & low margin items due to their disposable nature, and are purchased primarily based on cost. Therefore, the disclosed solution which incorporates the detection of biofilm formation will desirably incur a minimal expense both in terms of tooling costs and materials costs to the production of the device.

In some embodiments, a device suitable for biofilm detection is provided. The device includes a substrate and an indicating material disposed on the substrate, the indicating material including a hydration indicator. The device also includes a sealing layer disposed on the indicating material, the sealing layer comprising a biodegradable polymer that seals the indicating material from moisture. The sealing layer is biodegradable in the presence of a biofilm, allowing ingress of moisture to change a color of the hydration indicator. The indicating material may comprise a moisture-indicating substance that changes color upon hydration. The indicating materials may further comprise a hygroscopic binder. The binder may be selected from the group consisting of a carboxymethylchitosan hydrogel, carboxymethylcellulose, hydroxypropylmethylcellulose, and polyvinylpyrrolidone. In some embodiments, the biodegradable polymer is transparent and is selected from the group consisting of polylactic acid, polyvinyl acetate, polycaprolactone and polyvinyl chloride (PVC). The substrate in some embodiments is a container. In other embodiments, the substrate is a portion of an inner surface of a package for food, medicine or a medical device. In yet other embodiments, the substrate is a medical device for insertion into a subject. In some embodiments, the substrate may be a container. In some embodiments, the substrate may be a portion of an inner surface of a package for food, medicine or a medical device. In other embodiments, the sealing layer may be biodegradable in the presence of a biofilm, allowing ingress of moisture to change a color of the hydration indicator. In some embodiments, the substrate may be a medical device suitable adapted for insertion into a subject.

In some embodiments, a device suitable for insertion into a subject and suitable for biofilm detection is provided. The device includes a substrate comprising a medical device for insertion into a subject and an indicating material disposed on the substrate, the indicating material comprising a binder and a hydration indicator. The device also includes a sealing layer disposed on the indicating material, the sealing layer comprising a transparent biodegradable polymer that seals the indicating material from moisture. The substrate may be a body part or prosthesis for insertion into the subject. The indicating material may be a moisture-indicating substance that changes color upon hydration. The substrate for insertion into the subject may be an implantable medical device. In some embodiments, the sealing layer is subject to degradation by a biofilm, allowing ingress of moisture to change a color of the hydration indicator. The substrate may be selected from the group consisting of a catheter, a stent, a cannula, a prosthesis and a vascular access device. The sealing layer of the device is biodegradable in the presence of a biofilm formed on the second layer by at least one type of microorganism. In some embodiments, the sealing layer is biodegradable in the presence of a biofilm formed from one or more species selected from the group consisting of *E. coli, S. typhii, S. flexneri, S. aureus* and *V. cholera*. The sealing layer is biodegradable in the presence of a biofilm formed from one or more genera selected from the group consisting of *Escheria, Legionella, Staphylococcus, Streptocuccus, Salmonella, Shigella* and *Vibrio*.

In some embodiments, a method of using a medical device is provided. The method includes furnishing a medical device for insertion into a subject, the medical device comprising a first layer having a moisture-indicating substance and a transparent biodegradable sealing layer atop the first layer. The method also includes inserting or implanting the medical device into the subject, observing the first layer through the transparent biodegradable sealing layer; and observing a change in the first layer. In some embodiments, the change in the first layer is a change in a color of the first layer, visually observable through the transparent biodegradable sealing layer.

In some embodiments, a method of making a medical device is provided. The method includes furnishing a medical device for insertion into a subject and cleaning a surface of the medical device. The method also includes applying a hydration indicator to the surface of the medical device, sealing the hydration indicator with a transparent biodegradable polymer and curing or setting the transparent biodegradable polymer. In some embodiments, the surface of the medical device comprises an outer surface of the medical device. In some embodiments, the surface of the medical device comprises an inner surface of the medical device. In some embodiments, the step of applying the hydration indicator comprises applying the hydration indicator and a binder to the surface of the medical device. In some embodiments, the step of applying is accomplished by a method selected from the group consisting of dipping and spraying. In some embodiments, the step of sealing the hydration indicator with a transparent biodegradable polymer is accomplished by sealing with a transparent biodegradable polymer selected from the group consisting of polylactic acid, polyvinyl acetate, polycaprolactone and polyvinylchloride.

In some embodiments, a device for detecting a presence of a biofilm is provided. The device includes a substrate and an indicating material disposed on the substrate, the indicating material comprising a hydration indicator and a biodegradable polymer. The biodegradable polymer is subject to degradation by a biofilm, allowing ingress of moisture to change a color of the hydration indicator. In some embodiments, the device may include a sealing layer disposed on the indicating material, the sealing layer comprising a transparent biodegradable polymer that seals the indicating material from moisture. In some embodiments, the substrate comprises a medical device for insertion into a subject. In other embodiments, the substrate may be a package. The package may be intended for a medical device, a medicine, a food or other object for which the presence of a biofilm is highly undesirable. The substrate may also be a surface subject to contamination by microorganisms, and for which such contamination is also highly undesirable. The substrate may comprise a portion of a laboratory environment, a laboratory bench top, a laboratory machine or analytical instrument, and so forth.

In some embodiments, a device for detecting a presence of a biofilm is provided. The device includes a pouch made of a biodegradable polymer and an indicating material disposed within the pouch, the indicating material comprising a hydration indicator, wherein the biodegradable polymer is subject to degradation by a biofilm allowing ingress of moisture to change a color of the hydration indicator. In some embodiments, the indicating material also includes a binder. In some embodiments, the binder is hygroscopic and may be a carboxy-methylchitosan hydrogel, a carboxymethylcellulose material, a hydroxypropylmethylcellulose material or a polyvinylpyrrolidone material. In some embodiments, the indicating material may be a moisture-indicating substance that changes color upon hydration. In some embodiments, the device may include a layer of adhesive on a surface of the container for affixing the container to a package or a substrate. In some embodiments, the device may include a package to which the device is affixed. In some embodiments, the device may further include a substrate to which the device is affixed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device, comprising:
    a substrate;
    an indicating material disposed on the substrate, the indicating material comprising a hydration indicator; and
    a sealing layer disposed on the indicating material, the sealing layer comprising a biodegradable polymer that seals the indicating material from moisture present in a surrounding environment until the biodegradable polymer is breached, wherein the sealing layer is biodegradable in the presence of a biofilm, allowing ingress of moisture to change a color of the hydration indicator.

2. The device of claim 1, wherein the indicating material comprises a moisture-indicating substance that changes color upon hydration.

3. The device of claim 1, wherein indicating material further comprises a hygroscopic binder.

4. The device of claim 3, wherein the binder is selected from the group consisting of a carboxymethylchitosan hydrogel, carboxymethylcellulose, hydroxypropylmethylcellulose, and polyvinylpyrrolidone.

5. The device of claim 1, wherein the biodegradable polymer is transparent and is selected from the group consisting of polylactic acid, polyvinyl acetate, polycaprolactone and polyvinyl chloride (PVC).

6. The device of claim 1, wherein the substrate comprises a container.

7. The device of claim 1, wherein the substrate comprises a portion of an inner surface of a package for food, medicine or a medical device.

8. The device of claim 1, wherein the substrate comprises a surface of a laboratory equipment device.

9. The device of claim 1, wherein the substrate comprises a medical device for insertion into a subject.

10. A device, comprising:
    a substrate comprising a medical device for insertion into a subject;
    an indicating material disposed on the substrate, the indicating material comprising a binder and a hydration indicator; and
    a sealing layer disposed on the indicating material, the sealing layer comprising a transparent biodegradable polymer that seals the indicating material from moisture until the transparent biodegradable polymer is breached, wherein the sealing layer is subject to degradation by a biofilm, allowing ingress of moisture to change a color of the hydration indicator.

11. The device of claim 10, wherein the substrate comprises a body part or prosthesis for insertion into the subject.

12. The device of claim 10, wherein the indicating material comprises a moisture-indicating substance that changes color upon hydration.

13. The device of claim 10, wherein the substrate for insertion into the subject comprises an implantable medical device.

14. The device of claim 10, wherein the substrate is selected from the group consisting of a catheter, a stent, a cannula, a prosthesis and a vascular access device.

15. The device of claim 10, wherein the sealing layer is biodegradable in the presence of a biofilm formed on the sealing layer by at least one type of microorganism.

16. The device of claim 10, wherein the sealing layer is biodegradable in the presence of a biofilm formed from one or more species selected from the group consisting of *E. coli, S. typhii, S. flexneri, S. aureus* and *V. cholera.*

17. The device of claim 10, wherein the sealing layer is biodegradable in the presence of a biofilm formed from one or more genera selected from the group consisting of Escheria, *Legionella, Staphylococcus, Streptocuccus, Salmonella, Shigella* and *Vibrio.*

18. A method of using a medical device comprising:
    furnishing a medical device for insertion into a subject, the medical device comprising a first layer having a moisture-indicating substance and a transparent biodegradable sealing layer atop the first layer that seals the first layer from moisture until the transparent biodegradable sealing layer is breached, wherein the sealing layer is biodegradable in the presence of a biofilm, allowing ingress of moisture to change a color of the first layer;

inserting or implanting the medical device into the subject;

observing the first layer through the transparent biodegradable sealing layer; and observing the change in color of the first layer.

19. A method of making a medical device comprising:

furnishing a medical device for insertion into a subject;

cleaning a surface of the medical device;

applying a hydration indicator to the surface of the medical device;

sealing the hydration indicator with a transparent biodegradable polymer that seals the hydration indicator from moisture until the transparent biodegradable polymer is breached, wherein the transparent biodegradable polymer is subject to degradation by a biofilm, allowing ingress of moisture to change a color of the hydration indicator; and curing or setting the transparent biodegradable polymer.

20. The method of claim 19, wherein the surface of the medical device comprises an outer surface of the medical device.

21. The method of claim 19, wherein the surface of the medical device comprises an inner surface of the medical device.

22. The method of claim 19, wherein the step of applying the hydration indicator comprises applying the hydration indicator and a binder to the surface of the medical device.

23. The method of claim 19, wherein the step of applying is accomplished by a method selected from the group consisting of dipping and spraying.

24. The method of claim 19, wherein the step of sealing the hydration indicator with a transparent biodegradable polymer is accomplished by sealing with a transparent biodegradable polymer selected from the group consisting of polylactic acid, polyvinyl acetate, polycaprolactone and polyvinylchloride.

25. A device, comprising:

a substrate; and an indicating material disposed on the substrate, the indicating material comprising a hydration indicator, and a biodegradable polymer to seal the hydration indicator from moisture, the biodegradable polymer subject to degradation by a biofilm at least until breached, allowing ingress of moisture to change a color of the hydration indicator.

26. The device according to claim 25, further comprising a sealing layer disposed on the indicating material, the sealing layer comprising a transparent biodegradable polymer that seals the indicating material from moisture until the transparent biodegradable polymer is breached.

27. The device according to claim 25, wherein the substrate comprises a medical device for insertion into a subject.

28. A device, comprising:

a pouch comprising a biodegradable polymer; and an indicating material disposed within the pouch to seal the indicating material from moisture, the indicating material comprising a hydration indicator, wherein the biodegradable polymer is subject to degradation by a biofilm at least until breached, allowing ingress of moisture to change a color of the hydration indicator.

29. The device according to claim 28, wherein the indicating material further comprises a binder.

30. The device of claim 29, wherein the binder is hygroscopic and is selected from the group consisting of a carboxymethylchitosan hydrogel, carboxymethylcellulose, hydroxypropylmethylcellulose and polyvinylpyrrolidone.

31. The device of claim 28, wherein the biodegradable polymer is transparent and is selected from the group consisting of polylactic acid, polyvinyl acetate, polycaprolactone and polyvinyl chloride (PVC).

32. The device of claim 28, wherein the indicating material comprises a moisture-indicating substance that changes color upon hydration.

33. The device of claim 28, further comprising a layer of adhesive on a surface of the pouch for affixing the pouch to a package or a substrate.

34. The device of claim 28, further comprising a package to which the device is affixed.

35. The device of claim 28, further comprising a substrate to which the device is affixed.

* * * * *

UNITED STATES PATENT AND TRADEMARK OFFICE
CERTIFICATE OF CORRECTION

PATENT NO. : 9,535,043 B2
APPLICATION NO. : 14/130956
DATED : January 3, 2017
INVENTOR(S) : Manion et al.

Page 1 of 1

It is certified that error appears in the above-identified patent and that said Letters Patent is hereby corrected as shown below:

In the Specification

In Column 5, Lines 2-3, delete "single-layer coating 206" and insert -- single layer 206 --, therefor.

In Column 5, Line 36, delete "first layer 316." and insert -- first layer. --, therefor.

In Column 8, Line 18, delete "others. annatto," and insert -- others. Annatto, --, therefor.

In Column 10, Lines 2-3, delete "exposed layer 408" and insert -- innermost layer 408 --, therefor.

In Column 12, Line 49, delete "has an small" and insert -- has a small --, therefor.

In Column 12, Line 59, delete "polymer container 610 to" and insert -- polymer container to --, therefor.

In Column 13, Line 60, delete "indictor" and insert -- indicator --, therefor.

In Column 13, Lines 64-65, delete "moisture-indictor," and insert -- moisture indicator, --, therefor.

In Column 17, Lines 8-9, delete "*Streptocuccus*," and insert -- *Streptococcus*, --, therefor.

In Column 18, Line 52, delete "recitation no" and insert -- recitation, no --, therefor.

In Column 19, Line 7, delete "general such" and insert -- general, such --, therefor.

In Column 19, Line 14, delete "general such" and insert -- general, such --, therefor.

In the Claims

In Column 20, Line 60, in Claim 17, delete "Streptocuccus," and insert -- Streptococcus, --, therefor.

Signed and Sealed this
Sixth Day of February, 2018

Joseph Matal
*Performing the Functions and Duties of the
Under Secretary of Commerce for Intellectual Property and
Director of the United States Patent and Trademark Office*